(12) United States Patent
Laufer et al.

(10) Patent No.: US 7,783,332 B2
(45) Date of Patent: Aug. 24, 2010

(54) GLUCOSE MONITORING DEVICE AND METHOD

(76) Inventors: Michael Laufer, 1259 El Camino Real, #211, Menlo Park, CA (US) 94025; Daniel R. Burnett, 215 Valdez Ave., San Francisco, CA (US) 94127

( * ) Notice: Subject to any disclaimer, the term of this patent is extended or adjusted under 35 U.S.C. 154(b) by 1203 days.

(21) Appl. No.: 11/373,523

(22) Filed: Mar. 9, 2006

(65) Prior Publication Data
US 2006/0253003 A1    Nov. 9, 2006

Related U.S. Application Data

(60) Provisional application No. 60/660,176, filed on Mar. 9, 2005.

(51) Int. Cl.
*A61B 5/145*    (2006.01)
(52) U.S. Cl. .............. 600/319; 600/309; 600/316; 600/365
(58) Field of Classification Search .............. 600/309, 600/316, 319, 322, 365
See application file for complete search history.

(56) References Cited

U.S. PATENT DOCUMENTS

| | | | |
|---|---|---|---|
| 4,750,830 A | 6/1988 | Lee | |
| 5,713,353 A * | 2/1998 | Castano | 600/319 |
| 2003/0050544 A1 * | 3/2003 | Routt et al. | 600/318 |
| 2004/0087843 A1 * | 5/2004 | Rice et al. | 600/319 |
| 2005/0010091 A1 | 1/2005 | Woods et al. | |

FOREIGN PATENT DOCUMENTS

WO    03/037174    5/2003

* cited by examiner

*Primary Examiner*—Eric F Winakur
*Assistant Examiner*—Etsub D Berhanu
(74) *Attorney, Agent, or Firm*—Nixon Peabody LLP

(57) ABSTRACT

A method for determining the quantity of an analyte in a fluid is described along with various components of an apparatus designed to carry out the method. The method involves habituating a patient's eye to one or more colors, measuring the recovery time, and correlating the recovery time to the quantity of the analyte. A reproducible, objective, non-attentiveness-dependant test for assessing analyte levels is further disclosed. To this end, a device that measures saccadic eye movements may be used to assess the return of vision to the prehabituated state. The method and apparatus are particularly suited for noninvasively measuring blood glucose levels.

30 Claims, 10 Drawing Sheets

GLUCOSE MONITORING DEVICE AND METHOD

CROSS-REFERENCE TO RELATED APPLICATION

This application claims priority based on provisional application Ser. No. 60/660,176, entitled "GLUCOSE MONITORING DEVICE AND METHOD" by Michael Laufer and Daniel J. Burnett, filed on Mar. 9, 2005.

FIELD OF THE INVENTION

The present invention relates to the field of minimally invasive or noninvasive biochemical monitoring systems. More specifically, the present invention relates to noninvasive or minimally invasive glucose measuring devices.

BACKGROUND OF THE INVENTION

Diabetes is a group of diseases characterized by high levels of blood glucose resulting from defects in insulin production, insulin action, or both. Diabetes is the leading cause of blindness in people ages 20 to 70 and is sixth leading cause of death in the United States. Overall, the risk for death among people with diabetes is about 2 times that of people without diabetes. The disease often leads to other complications such as kidney, nerve and heart disease and strokes. It is the leading cause for non-traumatic amputations and kidney failure.

Diabetes is reaching epidemic proportions in the United States. There are approximately 18.2 million people in the United States, or 6.3% of the population, who have diabetes. While an estimated 13 million have been diagnosed with diabetes, 5.2 million people (or nearly one-third) are unaware that they have the disease. Furthermore, diabetes is one of the most common chronic diseases in children and adolescents; about 151,000 people below the age of 20 years have diabetes.

Diabetics must diligently monitor the glucose level in their blood. Blood glucose levels should be maintained between 80 to 120 mg/dl before meals and between 100-140 mg/dl at bedtime. Self-monitoring of blood glucose (SMBG) permits diabetics to know what their blood sugar level is so they can adjust their food, insulin, or activity level accordingly. Improved glucose control can forestall, reduce, or even reverse some of the long-term complications of diabetes.

The gold standard for testing blood glucose is the measurement of glucose in a plasma sample obtained from a vein. A drop of blood is placed on a small window in a teststrip. Blood glucose acts as a reagent in a chemical reaction that produces a color change or generates electrons. The color change is detected by a reflectance-meter and reported as a glucose value. Alternatively, the electrons generated in the reaction are detected as an electrical current and reported as a glucose value.

Problems with existing SMBG devices include the requirement of a drop of blood for each test (normally acquired through a prick of the finger). The blood sampling can be painful and cause calluses to form. It also increases the risk for warts and infections. The acute discomfort associated with this presents the largest barrier to life-saving blood glucose control.

Minimally invasive technologies currently on the market in the United States include the Gluco Watch® Biographer and the Guardian® Continuous Glucose Monitoring System.

The GlucoWatch® Biographer uses reverse iontolphoresis, which involves applying an electrical microcurrent to the skin. The current pulls sodium through the intact skin, with which the water follows the sodium and the water pulls glucose with it. The glucose concentration in this fluid is proportionate to the concentration in the blood.

However, there are several problems with this technology. There is a lag time of 20 minutes before a blood glucose value can be reported. The concentration of glucose in the fluid is only 1/1,000 of glucose in the blood. A mild skin discomfort last for a few minutes when the device is first applied to the skin. The device is intended for use only by adults (age 18 and older) with diabetes. It is intended to supplement, not replace, standard home blood glucose monitoring devices. The user also has to calibrate the Gluco Watch® Biographer with a blood glucose value measured on a traditional, i.e. "fingerstick," monitor. Thus a standard (invasive) blood glucose monitor is still required.

The Guardian® Continuous Glucose Monitoring System is designed to automatically and frequently monitor glucose values in subcutaneous interstitial fluid (ISF). It measures ISF glucose every five minutes and it has a hypoglycemia alert. Once inserted, the sensor is virtually painless, but it requires entry of glucose readings from a standard monitor at least twice a day in order to calibrate the sensor.

SUMMARY OF THE INVENTION

A solution is provided which recognizes that an analyte's concentration in blood is directly related to the recovery time of nerve function after stimulation to the point of attenuation, or habituation. A noninvasive or minimally invasive method for determining the quantity of an analyte in a fluid is described along with various components of an apparatus designed to carry out the method. The method involves habituating a patient's eye to one or more colors, measuring the recovery time, and correlating the recovery time to the quantity of the analyte. A reproducible, objective, non-attentiveness-dependant test for assessing analyte levels is also described. To this end, a device that measures saccadic eye movements to assess the return of vision to the prehabituated state is disclosed. The method and apparatus are particularly suited for noninvasively measuring blood glucose levels.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

DETAILED DESCRIPTION

Figure 1:
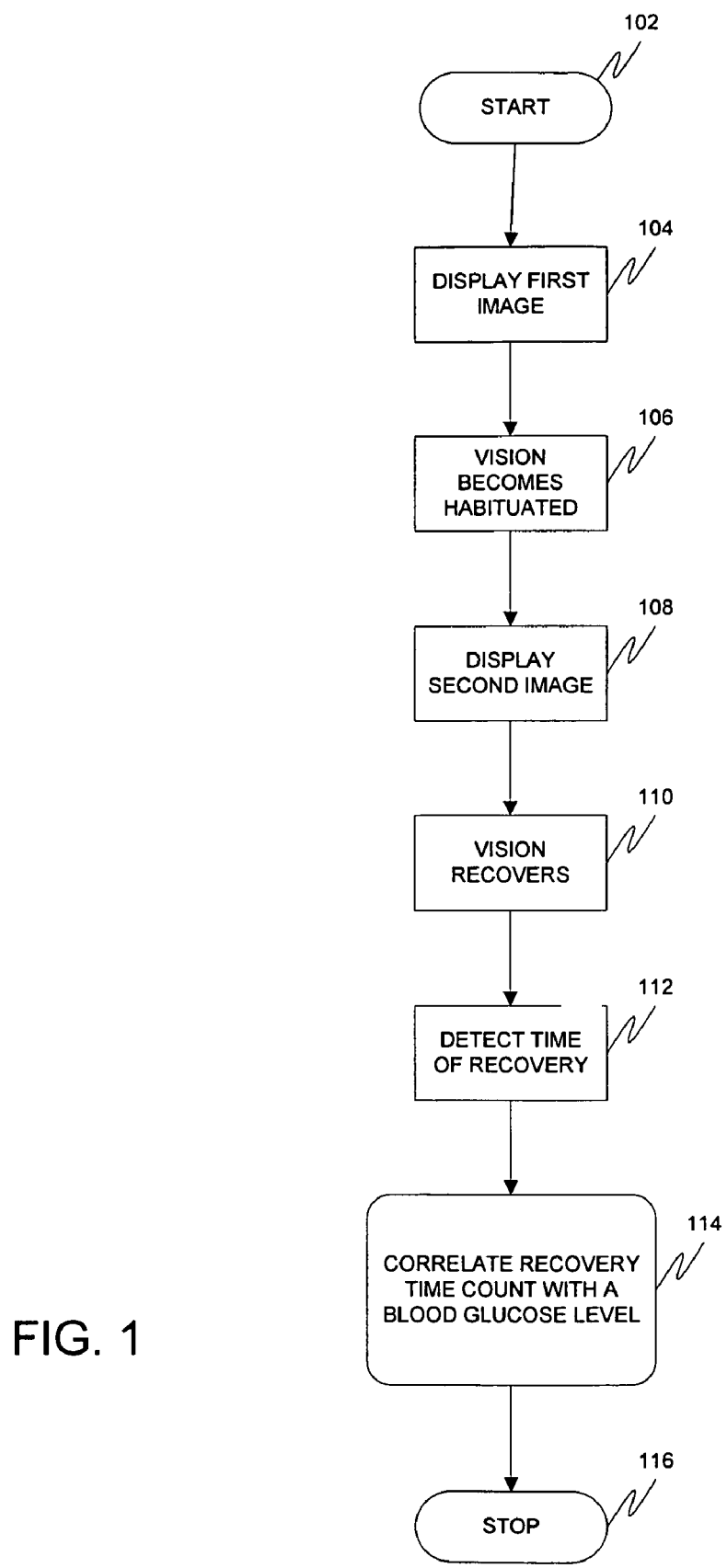
FIG. 1 is a flow diagram illustrating a method for measuring a blood glucose level.

Those of ordinary skill in the art will realize that the following detailed description of the present invention is illustrative only and is not intended to be in any way limiting. Other embodiments of the present invention will readily suggest themselves to such skilled persons having the benefit of this disclosure.

The present invention is based on a finding that glucose concentration in blood is directly related to the recovery time of nerve function after stimulation to the point of attenuation, or habituation. Applying this finding, blood glucose levels may be indirectly measured through a noninvasive or minimally invasive procedure. Other abnormalities related to deficiencies or surpluses in, for example, sodium, potassium, calcium and thyroid hormone levels can also be screened using the teaching of this invention, with appropriate time constant factors.

The vertebrate retina contains two kinds of light-sensitive neurons, rods and cones. Cones function in bright light and are responsible for color vision, whereas rods function in dim light and do not perceive color. Both rods and cones have two distinct cellular components: an outer segment, which contains dozens of membranous disks loaded with the membrane protein rhodopsin, and an inner segment containing the nucleus and many mitochondria, which produce the adenosine triphosphate (ATP) essential for phototransduction.

Like other neurons, rods and cones have a transmembrane electrical potential, produced by the electrogenic pumping of the $Na^+K^+$ ATPase in the plasma membrane of the inner segment. ATP in the inner segment powers the $Na^+K^+$ ATPase, which creates a transmembrane electrical potential by pumping 3 $Na^+$ out for every 2 $K^+$ pumped in. An ion channel in the outer segment also contributes to the membrane potential. This ion channel permits passage of either $Na^+$ or $Ca^{2+}$ and is gated, i.e., opened, by cGMP. The membrane potential is reduced by the flow of $Na^+$ and $Ca^{2+}$ back into the cell through cGMP-gated cation channels in the plasma membrane of the outer segment. The membrane potential is therefore determined by the net difference between the $Na^+$ and the $K^+$ pumped by the inner segment (which polarizes the membrane) and the influx of $Na^+$ through the ion channels of the outer segment (which tends to depolarize the membrane). When rhodopsin absorbs light, it triggers degradation of cGMP in the outer segment, causing closure of the cation channel. Without cation influx through the channel, the cell becomes hyperpolarized. The rods and cones form synapses with several ranks of interconnecting neurons that convey and integrate electrical signals. The signals then pass through the ganglion neurons to the optic nerve and then to the brain.

The photoreceptors are repolarized by the $K^+$ current and neurotransmitter secretion ceases.

Vision, whether color or contrast vision, is subject to attenuation and habituation by recurring, continuous or overwhelming stimulation. A camera flash, for instance, will temporarily blind a person by overwhelming the retinal nerve sensory transducers. The recovery time between stimulus and normal vision is related to $Na^+$ and $K^+$ transport. The inventors have discovered that the glucose gradient affects the rate of transport of $Na^+$ and $K^+$. This led to the important discovery that the recovery of nerves, e.g. the cones of the eye, is also directly correlated with glucose concentration.

The cones are commonly categorized into three types according to the photopigment they contain: (1) long wavelength or "red" cones (most sensitive to wavelengths around 565 nm); (2) middle wavelength or "green" cones (most sensitive to wavelengths around 530 nm); and (3) short wavelength or "blue cones" (most sensitive to wavelengths around 435 nm). The human ability to discriminate a spectrum of colors is based on these three different kinds of receptors. The perception of other colors arises from the combined stimulation of these elements. When all three types of cone cells are stimulated equally, the light is perceived as being achromatic or white.

Preferably, the present invention utilizes the principles described above to measure an analyte.

Reference will now be made in detail to implementations of the present invention as illustrated in the accompanying drawings. The same reference indicators will be used throughout the drawings and the following detailed description to refer to the same or like parts.

FIG. 1 is a flow diagram illustrating a method for measuring a blood glucose level. At 102, the method is initiated. At 104, a first image is displayed. Staring at the first image, for a period of time will result in attenuation or habituation, 106, of the first image's color. The person so stimulated is temporary blinded to that color. At 108, a second image, which may be a white background, is displayed. Instead of seeing white, the person will perceive the complementary color of the first color. This complementary color is a result of stimulation of only the nonattenuated cone cells.

Alternatively, the first image may be a recurrent pattern of black and white stripes. The second image may comprise a white or black area. To the habituated eye, a pattern opposite to the initial pattern appears, where white now appears black and vice versa.

After a period of time, vision recovers 110, and the time of recovery from habituation may be detected 112. At 114, the recovery time is correlated with a blood glucose level. The method may then be terminated 116.

Figure 2A:
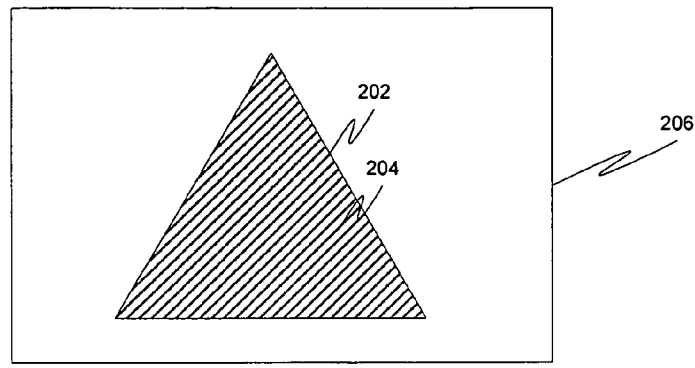
FIGS. 2a-d show examples of a display of an embodiment of an apparatus of the invention.

FIGS. 2a-d show examples of a display of an embodiment of an apparatus of the invention. FIG. 2a shows a first image 202, having a first color 204, displayed on a display module 206. The first image 202, in this embodiment, is a triangle. The first image 202 can be a mono-color or multiple colors or a pattern. The pattern can be, for example, animals, letters, numbers, stripes or the like. The first image 202 can be configured to be universally understood among cultures, languages and age groups.

Figure 2B:
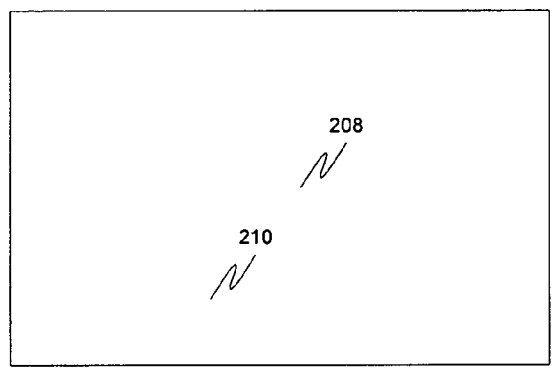
Figure 2C:
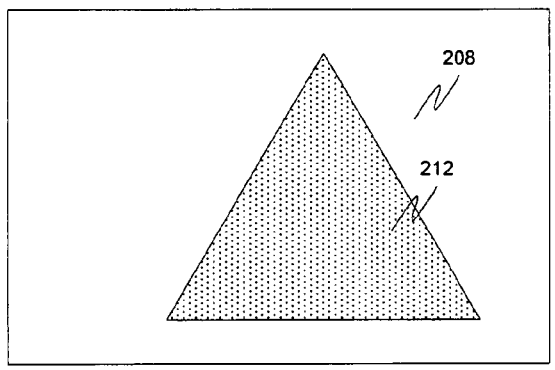

After a fixed period of viewing, preferably about 30 seconds, the first image 202 is replaced by a second image 208, the color white 210, as shown in FIG. 2b. As illustrated in FIG. 2c, to the habituated eye, the second image 208 appears to include a triangle in the complementary color 212 to first color 204. A time count can be initiated concurrently with initiation of the display of the second image 208.

Figure 2D:
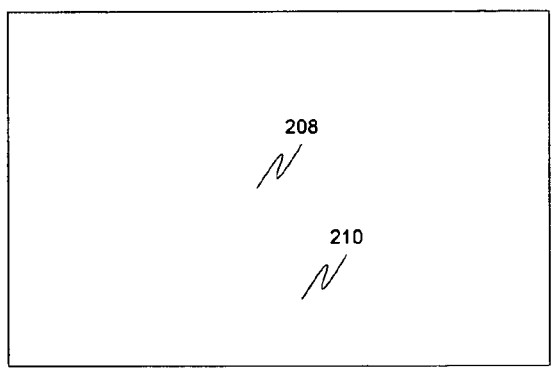

As illustrated in FIG. 2d, after a time period, the user's eye recovers and the second image 208 appears to be the color white 210. The time count is then terminated and the user's glucose level is determined using instructions that correlate time of recovery with a blood glucose level.

An embodiment of the present invention provides a reproducible, objective, non-attentiveness-dependant test for assessing analyte levels. To this end, a device that measures saccadic eye movements may be used to assess the return of vision to the prehabituated state. Saccadic eye movement is defined herein to mean the quick movement of the eye in going from one fixation point to another. Saccadic eye movements are normally involuntary and cannot easily be controlled by a patient. Typically, these movements are elicited clinically by moving a recurrent pattern in front of the patient. Eye movement tracking the pattern across the field of vision and back is a normal response.

The cornea of the eye is electrically positive relative to the back of the eye. Eye movement produces a moving (rotating) dipole source and, accordingly, signals that are a measure of the movement may be obtained. Eye movement may be measured by the placement of a pair of electrodes at the outside of the left and right eye (outer canthi). With the eye at rest the electrodes are effectively at the same potential and no voltage is recorded. The rotation of the eye results in a different potential, with the electrode in the direction of movement becoming positive relative to the second electrode. The signal can be calibrated by having the patient look nonselectively at two different fixation points located a known angle apart and recording the concomitant changes in electrical potential.

Eye motion can be detected, for example, with an electrooculogram (EOG) or by reflecting light off of the sclera and sensing the reflectance change as the eye moves.

Figure 3:
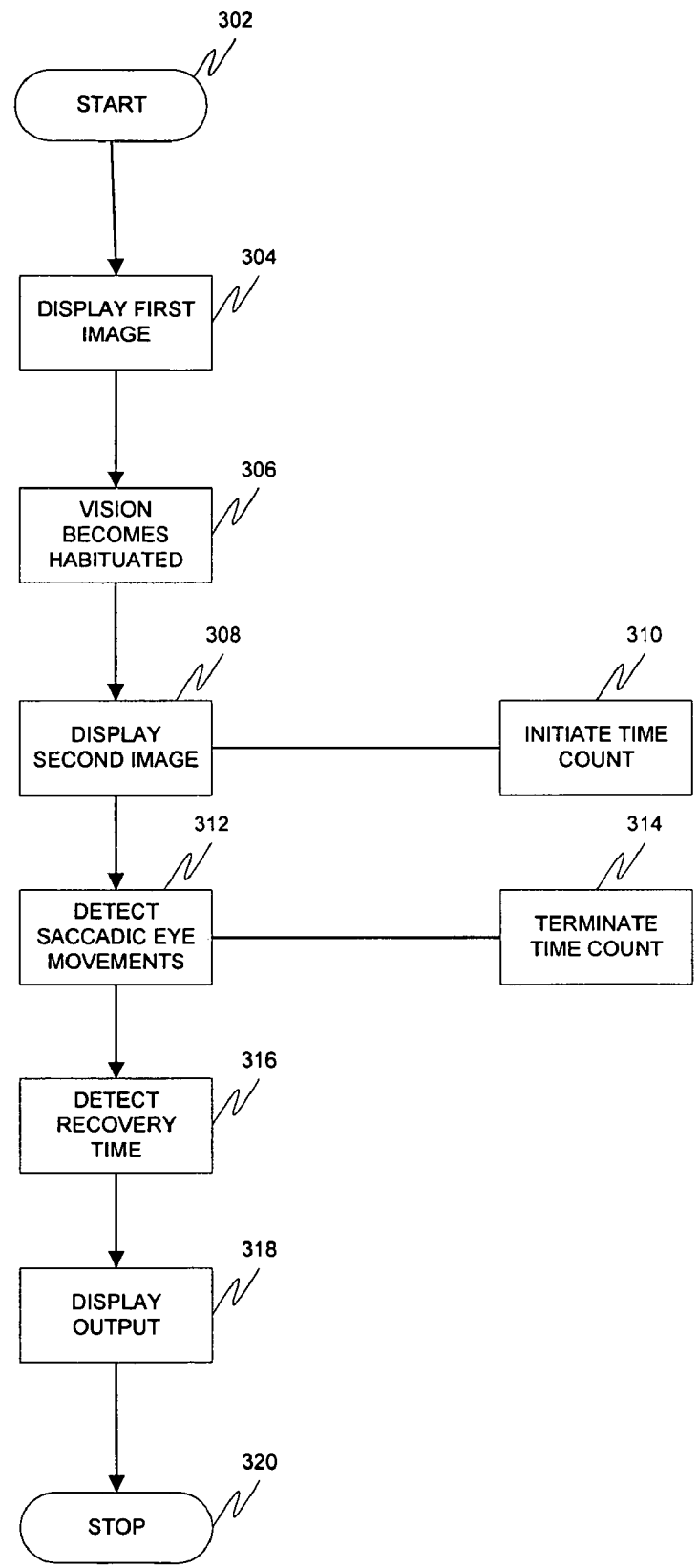
FIG. 3 is a flow diagram illustrating a method for measuring an analyte.

FIG. 3 is a flow diagram illustrating a method for measuring an analyte utilizing saccadic eye movement. At 302, the method is initiated. A first image is displayed 304. After a period of time, vision becomes habituated 306. A second image is displayed 308 and a time count is initiated 310. At 312, saccadic eye movements are detected. The time count is then terminated 314 and a recovery time can be detected 316. At 318, an output is displayed. The method can then be terminated 320.

Figure 4A:
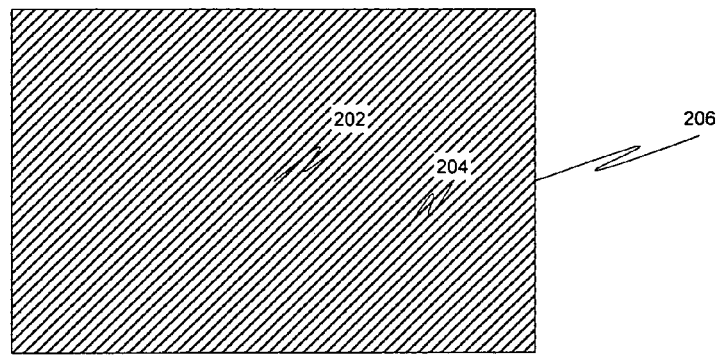
FIGS. 4a-d show examples of a display of an embodiment of an apparatus of the invention.
Figures 4B, 4C:
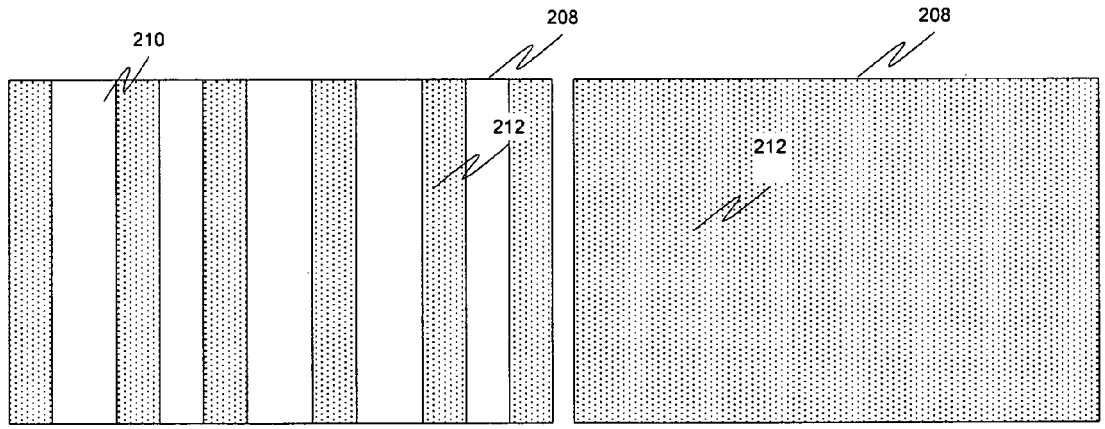

FIGS. 4a-d show examples of a display of an embodiment of an apparatus for measuring an analyte level utilizing saccadic eye movement. According to this embodiment, as shown in FIG. 4a, a first image 202 consisting of a first color 204, is displayed on a display module 206. After a fixed period of viewing sufficient for the user's eye to habituate to the first color 204, the first image 202 is replaced by a second image 208. The second image 208 comprises a repeating pattern of vertical stripes of the color white 210 alternating with stripes of the complementary color 212 to the first color 204, as illustrated in FIG. 4b. In an embodiment, the stripes move across the screen. As illustrated in FIG. 4c, to the habituated eye, the second image 208 appears to comprise entirely of the complementary color 212. A time count is initiated concurrently with initiation of the display of the second image 208.

Figure 4D:
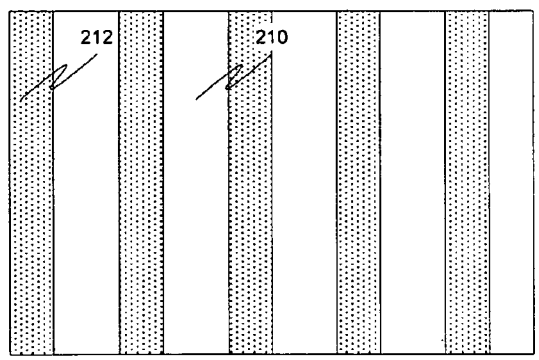

When the user's vision recovers, saccadic eye movements will occur because the user begins to see the stripes as stripes again, as illustrated in FIG. 4d. A device according to the present invention can be configured to allow a user to set the color and brightness so that the stripes are not seen until the recovery phase. Alternatively, the device can be programmed to self-configure based on early saccadic movements prior to when recovery could have occurred. In this way the device can be self-standardizing and calibrating.

The time between habituation and recovery is converted into a glucose level. This is then displayed and/or stored. In an embodiment, the glucose level is stored together with the corresponding date and time of measurement.

Figure 5:
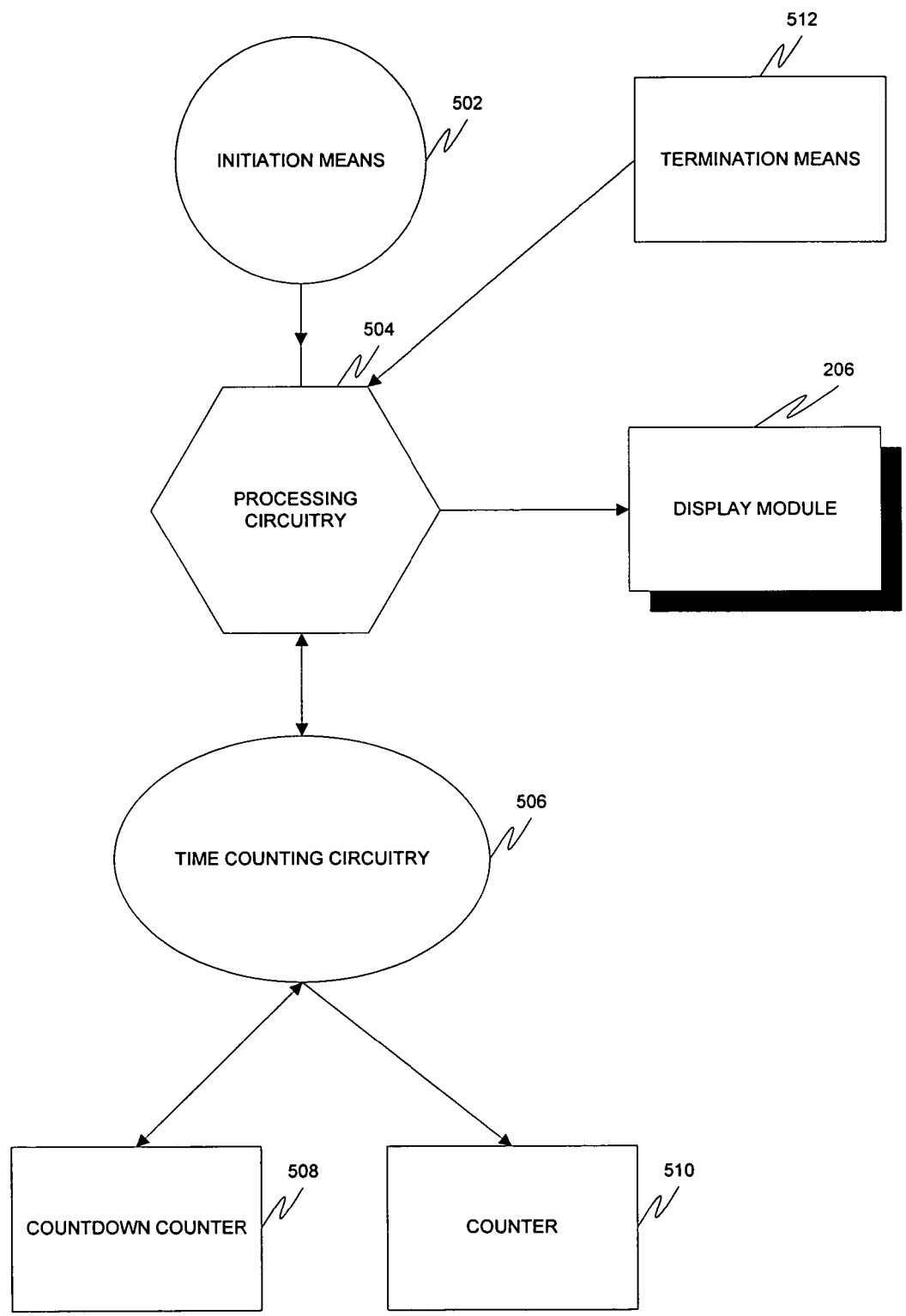
FIG. 5 is a block diagram of an embodiment of an apparatus of the invention.

In FIG. 5, there is presented a block diagram of an embodiment of an apparatus for measuring an analyte level consisting principally of an initiation means 502, processing circuitry 504, time counting circuitry 506, a countdown counter 508, a counter 510, a termination means 512, and a display module 206.

A user may turn the device on by pressing, pulling, turning, squeezing, or otherwise manipulating an initiation means 502. The initiation means 502 can be, but is not limited to, a button, knob, lever, switch, toggle, dial, or other similar user-manipulatable device. Processing circuitry 504 sends an initiation signal to the time counting circuitry 506 and to the display module 206. The display module 206 can be electronic, e.g., a CRT screen, or not electronic, e.g., a white board or piece of paper. The display module can comprise an alpha-numeric display and/or an audio means, such as a speaker.

The time counting circuitry 506 sends an initiation signal to the countdown counter 508. In some embodiments, the processing circuitry 504 sends a visual, audio, or vibrational signal indicating to the user that the test is about to start. This is especially appropriate if there is a delay between turning the device on and the initiation of the test. The display module 206 displays a first image.

The time counting circuitry 506 can be programmed with instructions for a countdown duration. In an embodiment, the countdown duration is about 30 seconds. After expiration of the countdown, the countdown counter 508 sends a termination signal to the time counting circuitry 506. The time counting circuitry 506 sends a termination signal to the processing circuitry 504. A signal is sent from the processing circuitry 504 to the display module 206 to terminate display of the first image.

The processing circuitry 504 sends an initiation signal to the display module 206 to display a second image and to the time counting circuitry 506. The time counting circuitry 506 sends a signal to the counter 510 to initiate a time count.

After recovery from habituation, a termination means 512 sends a signal to the processing circuitry 504. The termination means 512 can be a button, knob, lever, switch, toggle, dial, or other similar user-manipulatable device. In an embodiment of the invention, a user can press, pull, turn, squeeze, or otherwise manipulate the termination means 512 once the user believes that his eye has fully recovered from the habituated state. The initiation means 502 and termination means 512 can be the same device.

The processing circuitry 504 sends a termination signal to the time counting circuitry 506, which in turn sends a termination signal to the counter 510. The counter 510 sends a signal to the time counting circuitry 506 corresponding to the recovery time. The time counting circuitry 506 sends a signal corresponding to the recovery time to the processing circuitry 504. The processing circuitry 504 sends a signal to display module 206 to display an output. The output may comprise the recovery time.

Figure 6:
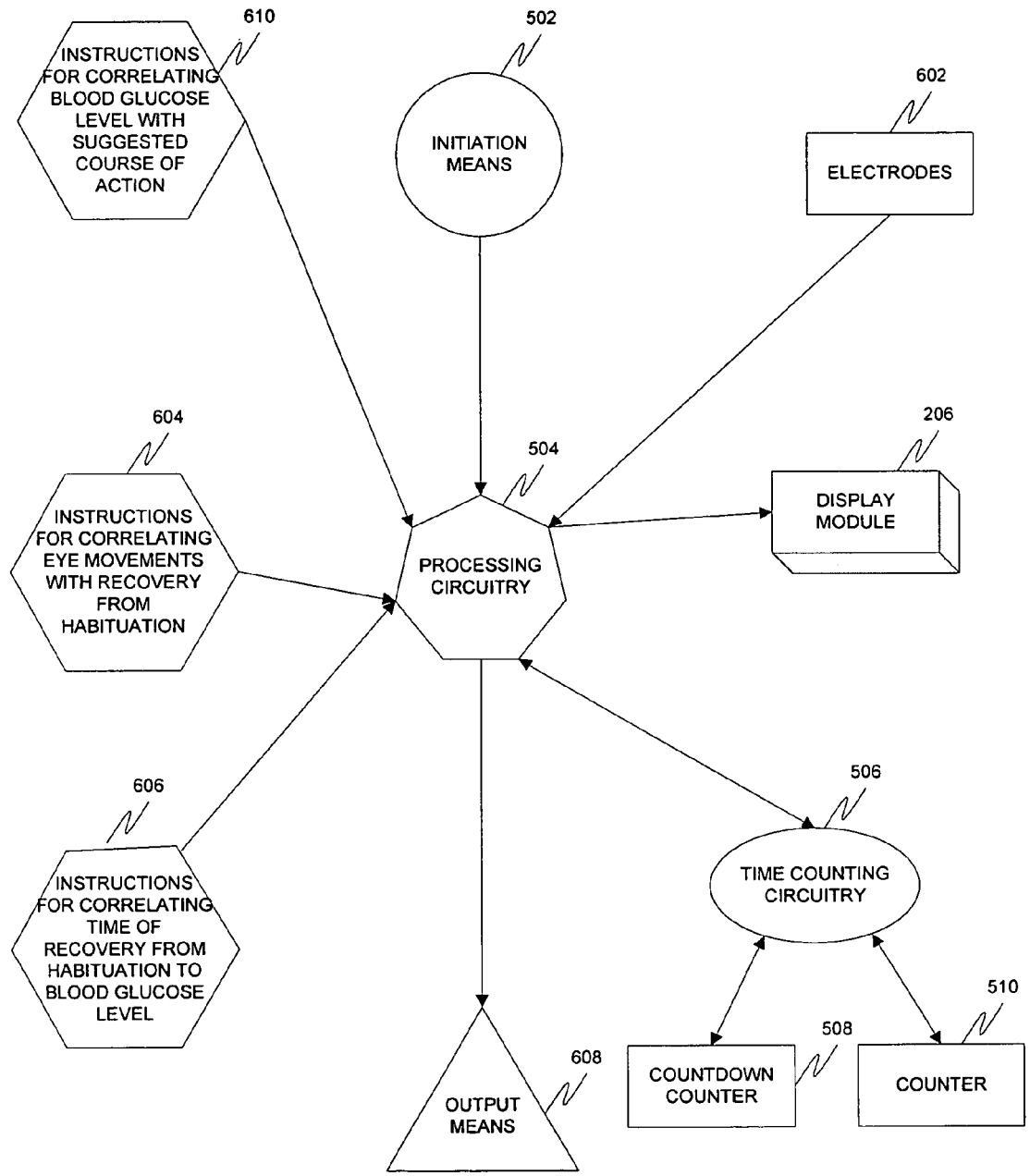
FIG. 6 is a block diagram of an embodiment of an apparatus of the invention.

FIG. 6 is a block diagram of a glucose monitoring device. According to the embodiment shown in FIG. 6, the termination means is a pair of electrodes 602. The electrodes 602 may be configured to attach to a user's head, the electrodes 602 produce electrical signals corresponding to the user's eye movement. The electrodes 602 are preferably configured to attach to a user's face in order to monitor the movement of facial and eye muscles associated with eye movement.

Processing circuitry 504 in this embodiment is programmed to receive electrical signals produced by the electrodes 602. Processing circuitry 504 may further be programmed with instructions for correlating eye movement with recovery from habituation 604. Processing circuitry 504 can be programmed to send a termination signal to the time counting circuitry 506 when it determines that the eye has recovered from habituation. Also, according to this embodiment, processing circuitry 504 can be programmed with instructions for correlating the recovery time to a blood glucose level 606 and to send signals corresponding to the user's blood glucose level to an output means 608. The output means 608 can be the display module 206. In another embodiment, the output means 608 is a separate display module. The output means 608 can comprise an audio means, such as a speaker.

In an embodiment, the apparatus can further comprise an input module. The input module can be, but is not limited to, a keyboard, mouse, nipple, trackball, speech recognition devise, or touch screen. In this embodiment, a user can input blood glucose measurements taken by a conventional blood test at about the same time that a glucose test performed with the present invention is conducted.

The memory of the apparatus can be initially void of any data that can be used to correlate a recovery time to a blood glucose level. A user can input data collected from a series of recovery time measurements, taken in accordance with the teaching of the current invention, and conventional blood tests taken at about the same time as the recovery time measurements. The apparatus can then use that data to correlate future recovery time measurements with blood glucose levels.

In an embodiment, if an apparatus has insufficient information on which to correlate a recovery measurement with a blood glucose level, it can display an output relating this fact to a user.

According to another embodiment, a user can from time to time calibrate an apparatus of the present invention by taking and entering data from recovery time tests and blood tests taken at about the same time as the recovery time measurements are taken.

Processing circuitry 504 can further be programmed with instructions on how to correlate a blood glucose level with a suggested course of action 610. Such instructions may be especially helpful for children and elderly users.

Figure 7:
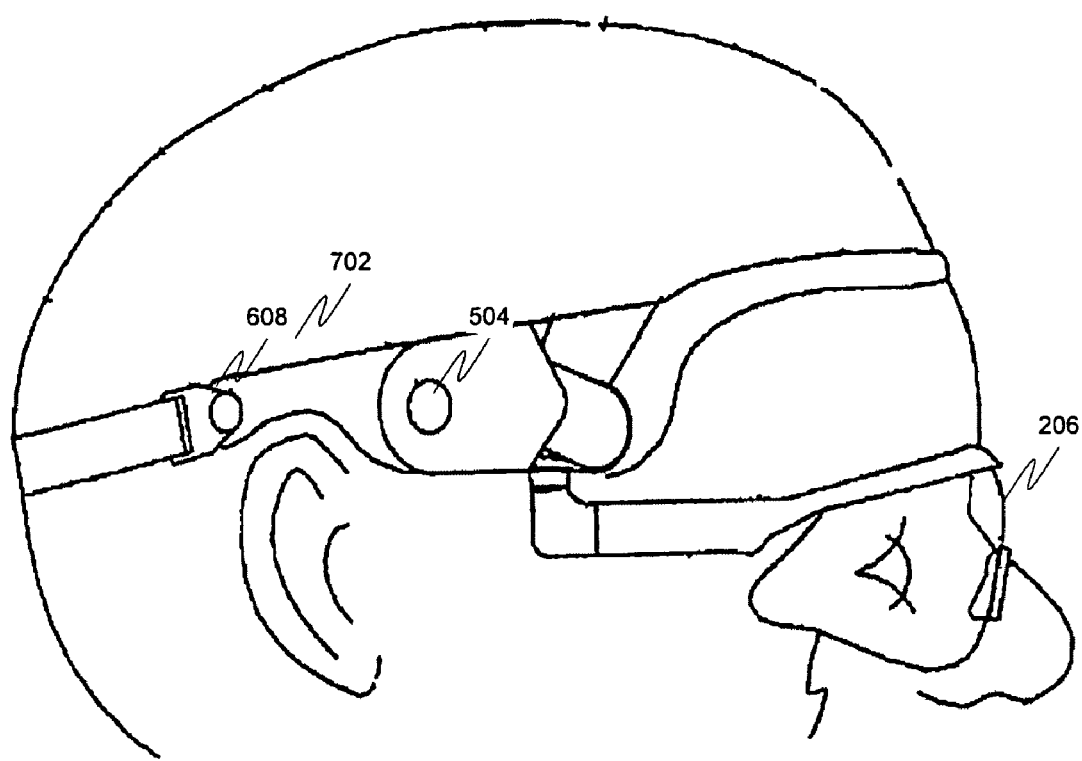
FIG. 7 shows a side view of an embodiment of an apparatus of the invention.

FIG. 7 shows a side view of an analyte monitoring device. According to this embodiment, the apparatus is a headpiece 702 configured to be worn by a user. "Headpiece," herein, is used to refer to any form of headgear that can be worn by a user to cover, at least partially, at least one eye. The headpiece can be of any shape or size, but is preferably lightweight. The headpiece can be, for example, eyeglasses, goggles, a helmet, binoculars, a monocular, a refractor, or an eye patch. In an embodiment, the headpiece is a helmet that blocks any external visual stimuli. The display module 206, processing circuitry 504, and output means 608 can be mounted on the headpiece. In another embodiment, the display module is mounted inside the headpiece and the processing circuitry is configured to plug into the headpiece.

In another embodiment, the headpiece comprises a display module without the processing circuitry. The headpiece can be configured so that a user can manually change the image displayed on the display module, e.g., by pressing a button, sliding a lever, etc. on the headpiece.

Figure 8:
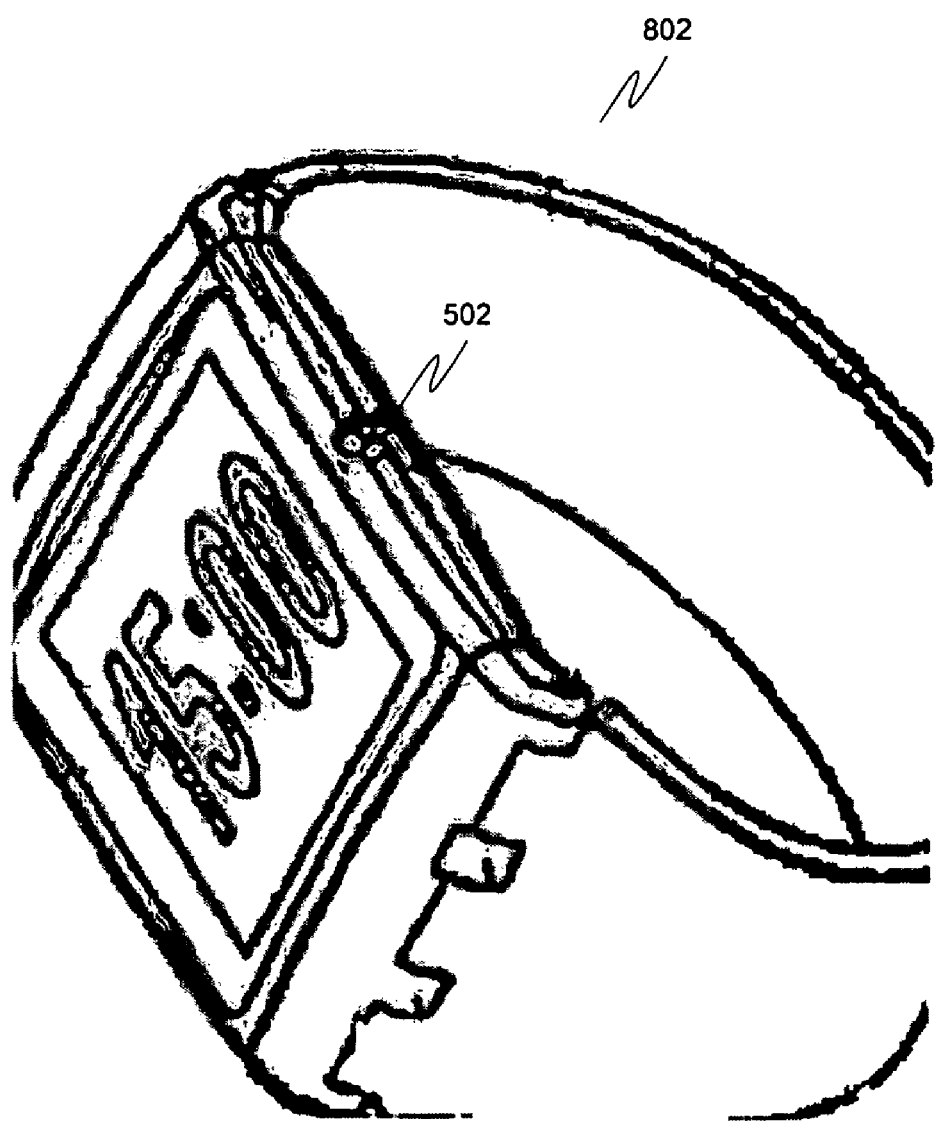
FIG. 8 shows a perspective view of an embodiment of an apparatus of the invention.

FIG. 8 shows a perspective view of an analyte monitoring device, wherein the apparatus is a watch 802 that can be worn by a user. The watch 802 can be changeable between an ordinary watch mode and an analyte measuring mode by a user manipulating initiation means 502. The watch can be similar in shape to an ordinary watch.

In conformity with the present invention, the apparatus may alternatively be configured to be worn around a user's neck or to be a hand held device that preferably fits in a user's pocket. A general purpose computer can also be used to carry out a method of the present invention.

Figure 9:
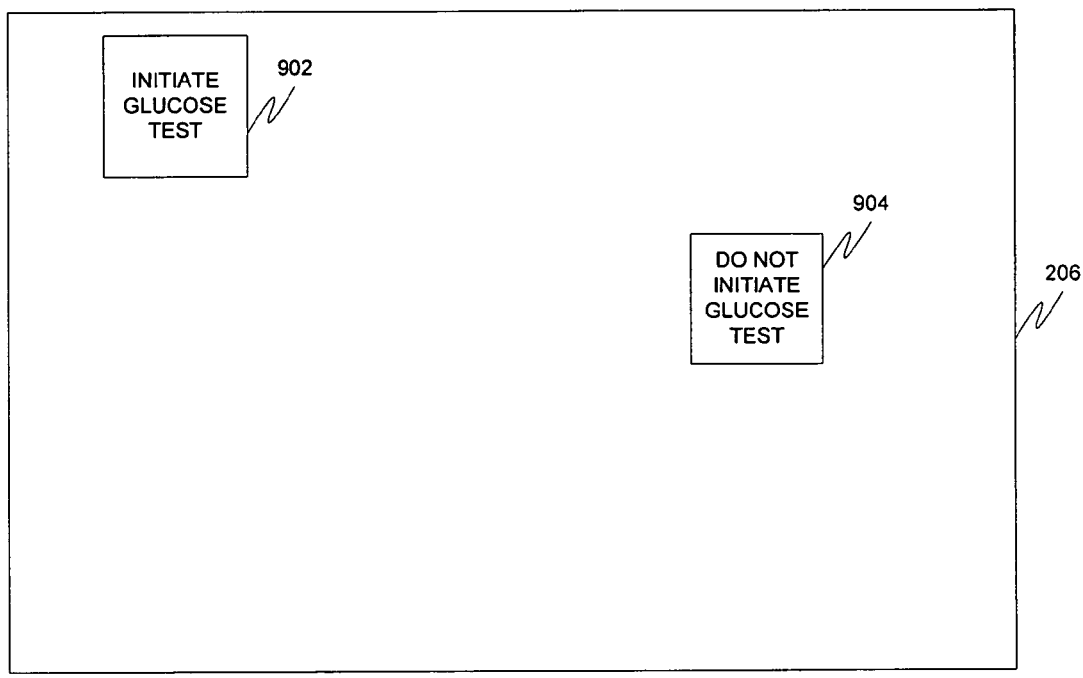
FIG. 9 shows an example of a display of an embodiment of an apparatus of the invention.

FIG. 9 shows an example of a display of an analyte monitoring device. Processing circuitry can be programmed to serve a dual function: to carry out a method of the present invention and to automatically switch a general purpose computer from an operative mode to a screensaver mode when a period of inactivity exceeds a predetermined time period. In this way, a user can be reminded to periodically check his/her glucose level throughout the day, and especially after lunch. A mouse, trackball, nipple, touch screen, keyboard, button or other similar devise can be used as an initiation means. As illustrated in FIG. 7, processing circuitry can be programmed to prompt a user to click on an "initiate" 902 or "do not initiate" 904 icon. If the user clicks on the initiate icon 902, processing circuitry can send an initiation signal initiating a test as described above.

In an embodiment, processing circuitry is programmed to remind a user at regular intervals, or at times that can be entered by the user, to check her glucose level. The processing circuitry can be programmed to display a pop-up window, vibrate, or sound an alarm.

Figure 10A:
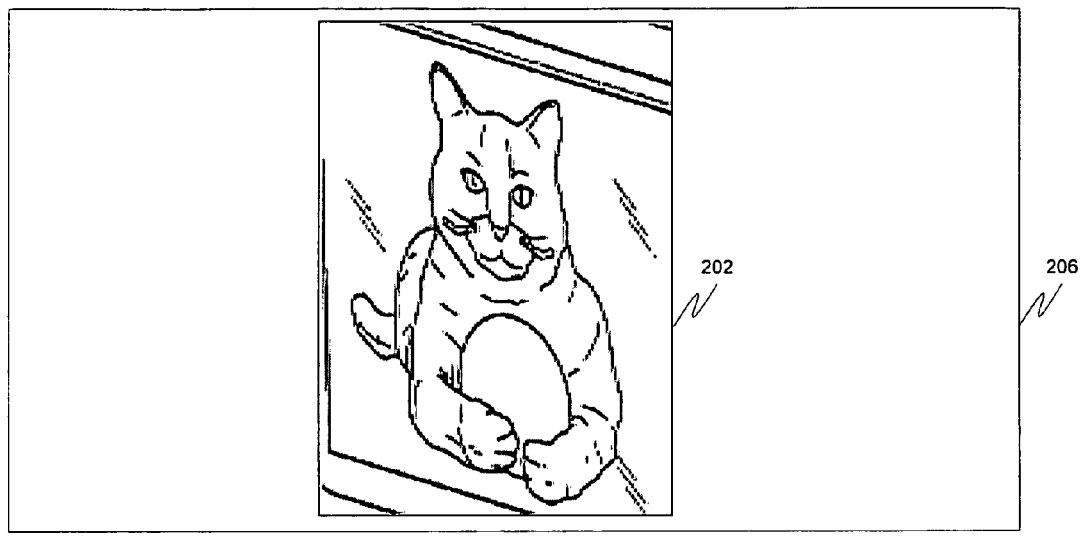
FIGS. 10a-b show examples of a display of an embodiment of an apparatus of the invention.
Figure 10B:
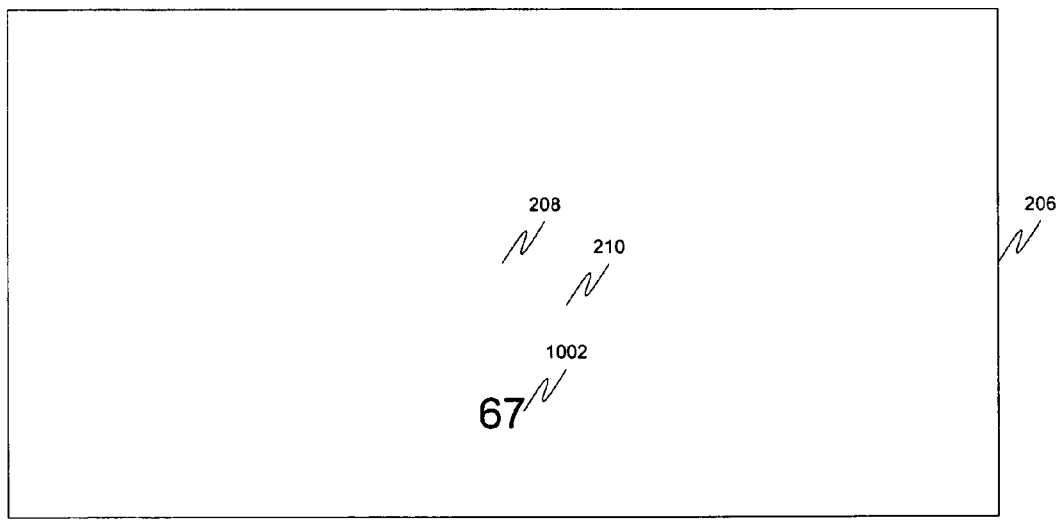

FIGS. 10a-b show examples of a display of an analye monitoring apparatus. As illustrated in FIG. 10a, the present invention can be adapted for group screening of glucose levels. According to one embodiment, a first image 202 is displayed on a display module 206, appropriately configured for group screening, for a fixed period of time. As illustrated in FIG. 10b, second image 208, which can be the color white 210, is then projected on the display module 206, together with a number count 1002. When an audience member's eye becomes unhabituated, he can get an approximate glucose level by looking at what number 1002 is displayed at the time his vision recovers.

Similarly, in accordance with the present invention, software can be distributed or images described previously could be broadcast on mass media or available on the Internet that would allow rapid screening of many individuals. Children, for instance, could be quickly and painlessly screened for abnormal glucose levels.

An individual was tested using an embodiment of the present invention as follows. Processing circuitry was programmed in BASIC and C++ to send a signal to a computer screen to display the color magenta for 30 seconds. The processing circuitry then sent a signal to the computer screen to change the display to alternating bands of cyan (the complementary color to magenta) and white. A time count was initiated. The cyan and white stripes were alternated at a frequency of about 10 Hz. To the user, the screen appeared entirely cyan until the user's vision recovered. After recovery, the screen appeared to have stripes of magenta alternating with cyan that moved across the screen. The time count was terminated when the stripes were visible to the user. This period was compared at different glucose levels. Glucose levels were independently measured with a calibrated handheld glucometer. Glucose levels in the tested individual were manipulated by having him ingest a highly-sugared solution. Also, a dose of glucagons was injected to increase the glucose level. A period of hypoglycemia was noted about thirty minutes after the glucagons injection. The length of the recovery period was correlated with the glucose levels measured and are shown in table 1.

TABLE 1

| Recovery Period (seconds) | Measured Glucose Level (mg/dL) |
|---|---|
| 28 | 210 |
| 28 | 210 |
| 35 | 150 |
| 37 | 150 |
| 47 | 110 |
| 48 | 110 |
| 55 | 85 |
| 56 | 85 |

By using the method and apparatus of the present invention, a user can indirectly measure an analyte level by measuring the recovery time of the user's eye after stimulation to the point of habituation. Advantageously, the method and apparatus allow a diabetic to measure his glucose level without having to prick a finger, thereby improving the chances of diligent monitoring of blood glucose levels.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for measuring the concentration of an analyte in a body fluid, comprising:
    displaying a first image, having a first color, on a display module to a user viewing the display module for an amount of time sufficient to cause the user's eye to habituate from a first state to a habituating state in response to viewing the color for a period of time;
    replacing the first image with a moving second image on the display module;
    measuring a recovery time of the user's eye from the habituating state to the first state based on a movement of the user's eye; and
    correlating the recovery time to an analyte concentration to measure the analyte of the user.

2. The method of claim 1, wherein the first image is displayed for about 30 seconds.

3. The method of claim 1, wherein the first image is a universally recognized character.

4. The method of claim 1, wherein the second image comprises stripes and is configured to move across the display module.

5. The method of claim 4, wherein the stripes comprise white stripes and stripes complementary in color to the first color.

6. The method of claim 1, wherein the second image is the color white.

7. The method of claim 1, wherein the analyte is glucose.

8. The method of claim 1, further comprising correlating the analyte concentration with suggested user instructions and displaying said instructions.

9. The method of claim 1, wherein the measuring of the recovery time further comprises detecting eye movement.

10. The method of claim 9, wherein the detecting of the eye movement is performed by at least one sensor electrode in contact with the user's face.

11. The method of claim 1, wherein the measuring of the recovery time further comprises detecting a termination signal generated by the user's manipulation of a termination means.

12. The method of claim 1, wherein a time count is displayed contemporaneously with the second image.

13. A method for measuring an analyte concentration in a vertebrate comprising:
    displaying a color to a vertebrate's eye via a display module over a period of time;
    detecting saccadic eye movements using a sensor to determine a recovery time from when the movement of the eye returns from a habituated state to a first state; and
    correlating the recovery time to an analyte concentration to measure the analyte concentration of the vertebrate.

14. The method of claim 13, further comprising:
    displaying a first image on the display module for an amount of time sufficient to habituate vision of the vertebrate;
    replacing the first image with a moving second image;
    initiating a time count;
    terminating a time count; and
    displaying an output based on the recovery time.

15. The method of claim 14, further comprising recording and storing the output.

16. The method of claim 13, wherein the analyte is glucose.

17. The method of claim 16, further comprising recording a blood glucose concentration detected at a time substantially contemporaneous with the method through blood sampling.

18. The method of claim 13, wherein the detecting of the saccadic eye movements further comprises measuring eye movements using an electroocculogram.

19. The method of claim 13, wherein the detecting of the saccadic eye movements further comprises reflecting light off of the user's sclera, detecting a reflectance, and detecting a change in the reflectance.

20. The method of claim 13, wherein correlating the recovery time to an analyte concentration further comprises correlating the recovery time to an analyte concentration based on data previously input by the user.

21. The method of claim 20, wherein the data previously input by the user comprises:
    data collected from blood sampling; and
    a recovery time measurement, wherein the blood sampling is taken substantially contemporaneously with the recovery time measurement.

22. An apparatus for measuring an analyte level in a user, the apparatus comprising:
    a display module configured to display a first image;
    a circuit coupled to the display module, the circuit configured to cause the display module to display a moving second image after an amount of time sufficient to habituate a user's eye to the first image from a first state to a habituated state, wherein the second image is configured to appear distinct from the first image when the user's eye is in the habituated state; and
    a sensor coupled to the circuit, the sensor configured to monitor saccadic eye movements of the user's eye to determine a recovery time from the habituated state to the first state based on a movement of the user's eye, the circuit configured to correlate the recovery time to an analyte concentration of the user.

23. The apparatus of claim 22, wherein the apparatus further comprises:
    an initiation means; and
    time counting circuitry, wherein the time counting circuitry is programmed to send a termination signal to the processing circuitry after an amount of time sufficient to permit the user's eye to habituate.

24. The apparatus of claim 22, wherein the analyte is glucose.

25. The apparatus of claim 22, further comprising an input means, wherein the input means is configured to permit a user to input recovery time measurements and corresponding analyte levels, wherein the analyte level is measured substantially contemporaneously with a recovery time measurement through a means other than a recovery time measurement.

26. The apparatus of claim 22, further comprising a storage module configured to store data input by the user.

27. The apparatus of claim 26, wherein the storage module is further configured to store a schedule input by the user and wherein the display module is further configured to display an output according to the schedule requesting that an analyte level be entered by the user.

28. The apparatus of claim 26, wherein the circuit is further configured to display an output requesting that an analyte level from another analyte sensing source be entered according to a predetermined schedule.

29. The apparatus of claim 22, wherein the apparatus is a headpiece.

30. The apparatus of claim 29, wherein the headpiece is a refractor.

\* \* \* \* \*